(12) United States Patent
Ericson et al.

(10) Patent No.: US 7,044,002 B2
(45) Date of Patent: May 16, 2006

(54) METHOD AND DEVICE FOR MONITORING THE FLOW SPEED OF AN INFUSION SOLUTION

(75) Inventors: Björn Ericson, Lund (SE); Ola Neckling, Malmö (SE)

(73) Assignee: Ganbro Lundia AB, Lund (CH)

( * ) Notice: Subject to any disclaimer, the term of this patent is extended or adjusted under 35 U.S.C. 154(b) by 640 days.

(21) Appl. No.: 10/258,015

(22) PCT Filed: Apr. 17, 2001

(86) PCT No.: PCT/SE01/00837

§ 371 (c)(1),
(2), (4) Date: Dec. 17, 2002

(87) PCT Pub. No.: WO01/78808

PCT Pub. Date: Oct. 25, 2001

(65) Prior Publication Data

US 2004/0025597 A1    Feb. 12, 2004

(30) Foreign Application Priority Data

Apr. 19, 2000    (SE) .................................... 0001445

(51) Int. Cl.
    *G01F 1/37*    (2006.01)
    *A61M 31/00*    (2006.01)
(52) U.S. Cl. .................................... 73/861.52; 604/65
(58) Field of Classification Search ............. 73/861.52; 604/65

See application file for complete search history.

(56) References Cited

U.S. PATENT DOCUMENTS

| 3,640,277 A | * | 2/1972 | Adelberg ..................... 604/141 |
| 5,059,182 A | * | 10/1991 | Laing ......................... 604/142 |
| 5,356,378 A | | 10/1994 | Doan |
| 5,792,367 A | | 8/1998 | Mattisson et al. |
| 5,904,666 A | | 5/1999 | DeDecker et al. |

FOREIGN PATENT DOCUMENTS

| EP | 0 565 485 | 10/1993 |
| EP | 1 276 522 B1 | 1/2005 |

\* cited by examiner

*Primary Examiner*—Harshad Patel
(74) *Attorney, Agent, or Firm*—Finnegan, Henderson, Farabow, Garrett, & Dunner, L.L.P.

(57) ABSTRACT

Method and device for monitoring the flow speed of an infusion solution, such as with hemofiltration or hemodiafiltration. The device has a tube for conducting an infusion solution from a source of infusion solution to a pump device in the form of a metering pump, such as a peristaltic pump or a ceramic pump, and on to an infusion device, such as a drip chamber. The flow speed is determined by the metering pump. The flow speed is monitored separately in that the pressure across a restriction device in the tube is measured. The restriction device can be a separately arranged restriction valve. Alternatively the restriction device is arranged by the tube having a small internal diameter of the order of 0.5 mm in size. The pressure measuring device only needs to measure the absolute pressure with respect to the atmosphere. The hydrostatic pressure due to the infusion bag being hung above the pump and the pressure meter is subtracted in a calculation device.

17 Claims, 4 Drawing Sheets

METHOD AND DEVICE FOR MONITORING THE FLOW SPEED OF AN INFUSION SOLUTION

CROSS REFERENCE TO RELATED APPLICATIONS

This application is a national phase application based on PCT/SE01/00837, filed Apr. 17, 2001, the content of which is incorporated herein by reference and claims the priority of Swedish Patent Application No. 0001445-6, filed Apr. 19, 2000, the content of which is incorporated herein by reference.

FIELD OF THE INVENTION

The invention relates to a method and a device for monitoring the flow speed of an infusion solution, such as with hemofiltration or hemodiafiltration.

PRIOR ART

With hemofiltration, blood is extracted from the patient to be treated in an extracorporeal blood path. The blood path comprises a hemo-filter with a semi-permeable membrane, through which passes plasma among other things. The plasma is replaced by an infusion solution which is normally supplied after the hemo-filter, so-called post-infusion. In certain applications pre-infusion is also used. Before the blood is passed back to the patient it passes through a drip chamber where any air bubbles are separated. The infusion solution is normally added to this drip chamber.

During treatment by hemofiltration, the blood of the patient having a reduced kidney function or no kidney function at all is cleaned. Decomposition products such as urea and creatinine are removed, electrolytes such as sodium, potassium, calcium and magnesium are normalised and balanced, buffer substances such as bicarbonate or acetate are supplied and fluid is removed. The treatment normally takes place in a dialysis clinic three times a week, for about 3–6 hours each time.

Alternatively, the treatment used to clean the blood can be hemodiafiltration, peritoneal dialysis or hemodialysis.

The infusion solution is often provided in bags with sterile infusion solution having the desired composition, which corresponds to the composition of the plasma but with certain corrections. The bags normally have a size of 2–5 liters. Often, more than one bag per treatment is used.

Alternatively the infusion solution is supplied on-line by being made in situ with the aid of a dialysis machine or other apparatus for preparation of sterile solution or solution for infusion, especially when larger volumes of infusion solution are required, such as 10–100 liters per treatment.

With hemodiafiltration and hemofiltration, the volume of the infusion solution which is supplied to the patient must exactly compensate for the volume of plasma which is extracted from the blood. Normally however it is desired to remove a certain amount of fluid from the patient who cannot get rid of excess fluid via urine. Thus, slightly less volume of infusion solution is added than the volume of plasma which is disposed of, whereby the difference corresponds to the desired volume of fluid which is to be extracted from the patient.

It is therefore necessary to know the fluid balance accurately. The volume of plasma which is disposed of is accurately measured by the hemofiltration machine and the added volume of infusion solution is measured by the pump device which supplies the infusion solution.

Normally the latter pump device is constituted by a peristaltic pump, where one or more rollers, positioned on a rotor, act on a semi-circular formed segment of a plastic tube in order to clamp it and thereby impel the fluid in the tube. In such a peristaltic pump device the flow speed is proportional to the rotational speed of the rotor. Thus normally the rotational speed is taken as a measure of the flow speed of the infusion solution.

If however the tube which leads from the source of the infusion solution, normally one or more bags, becomes pinched or totally blocked, the peristaltic pump will pump the infusion solution at a lower speed or not at all. If this is not discovered, the result can be that the blood of the patient becomes concentrated and the blood volume is reduced.

The peristaltic pump's pump segment is manufactured of a plastic tube of PVC, and it is well known that the dimensions of such a plastic tube have large tolerances. These tolerances directly affect the determination of the flow speed. In this way a systematic error can be present which can be large enough to cause problems.

A first object of the present invention is to allow monitoring that a constriction or total stop is not present in the flow of infusion fluid.

A second object of the invention is to measure the infusion flow with a device separate from the peristaltic pump in order to check that too large a deviation is not present, for example due to tolerances.

A third object of the invention is to allow calibration of the pump segment prior to the treatment.

SUMMARY OF THE INVENTION

Therefore according to the invention a method and device are provided for monitoring the flow speed of an infusion solution, such as with hemofiltration or hemodiafiltration. The device comprises a tube for conduction of an infusion solution from a source of infusion fluid to a pump device, as well as a pump device for pumping the infusion fluid to an infusion device such as a drip chamber. According to the invention, the flow speed is monitored by measuring the pressure drop across a restriction device arranged in the tube.

The pump is suitably a metering pump for metering the infusion solution, such as a peristaltic pump or a ceramic pump. The source of infusion solution is constituted by one or more bags with sterile infusion solution, such as hemofiltration solution. There is a hanging device for arranging the bags at a particular height with respect to the pressure measurement device. In this way the pressure measurement device can measure the pressure with respect to the surrounding atmosphere, upon which a calculation device calculates the pressure drop as well as the measured pressure corrected for the hydrostatic pressure due to said height.

BRIEF DESCRIPTION OF THE DRAWINGS

Further objects, features and advantages of the invention will be clear from the following detailed description of a preferred embodiment of the invention with reference to the accompanying drawings.

DESCRIPTION OF EMBODIMENTS OF THE INVENTION

Figure 1:
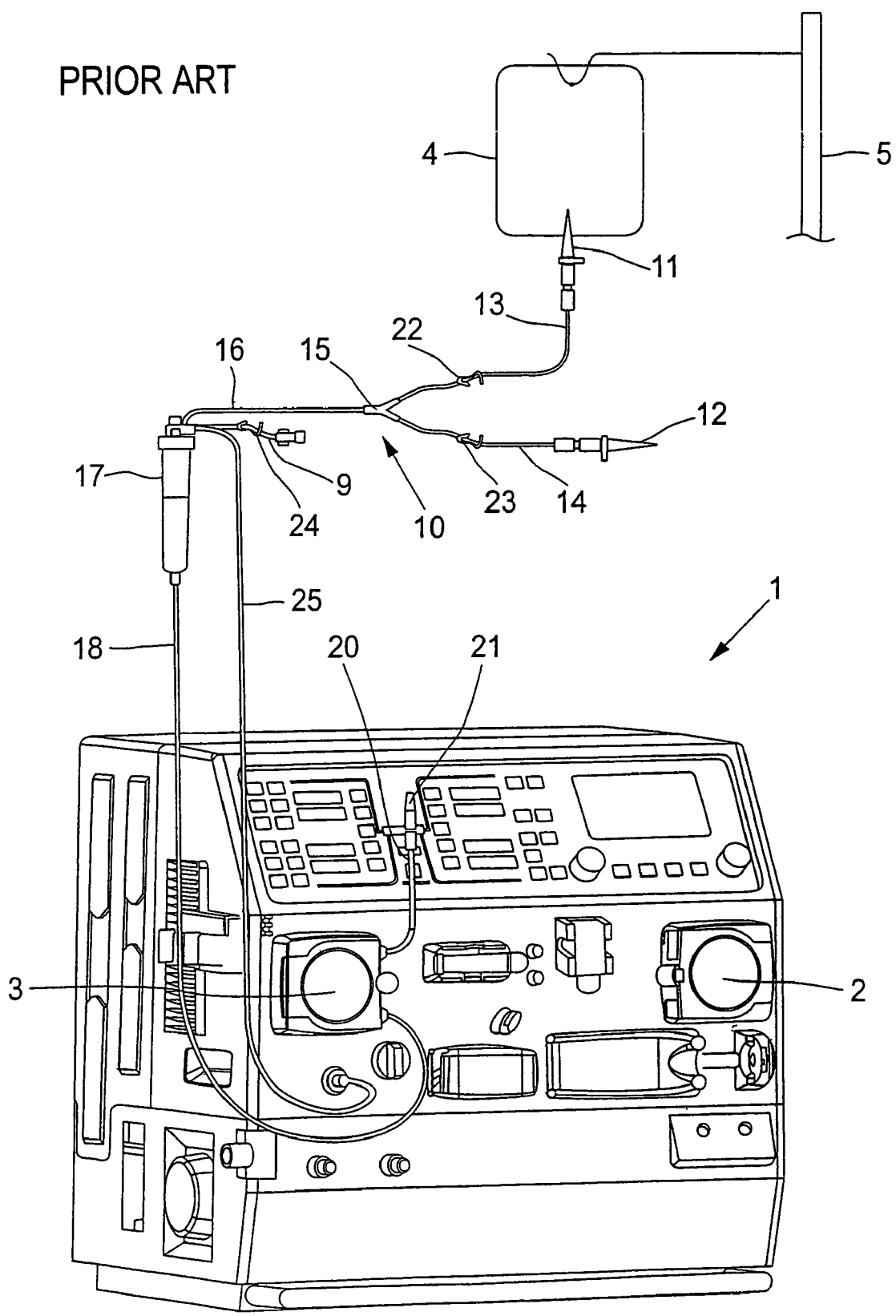
FIG. 1 is a schematic plan view of a prior art hemofiltration apparatus.

FIG. 1 shows a known hemofiltration apparatus of the AK200 type, which is manufactured and sold by Gambro Lundia AB, Lund, Sweden. The hemofiltration apparatus 1 comprises two peristaltic pumps 2 and 3, of which the first pump is used to pump blood in a non-depicted extracorporeal circuit, and the second pump 3 is used to pump infusion solution from a source in the form of a storage bag 4 suspended on a stand 5, which can be fixed to the apparatus 1.

The infusion tube set 10 consists of two connectors 11 and 12 each connected with its own tube 13, 14. The tubes 13 and 14 are connected with each other via a Y-coupling 15, which is also connected with a tube 16 that leads to a drip chamber 17. A tube 9 ending in a connector leads to the upper end of the drip chamber, for possible supply of medicament or other fluid to the drip chamber.

From the bottom of the drip chamber a tube 18 leads to a pump segment 19 positioned in the peristaltic pump 3. A tube 20 leads from the other end of the pump segment 19 to a connector 21, intended to be coupled to a connection to the extracorporeal circuit.

The tubes 13, 14 and 9 are provided with tube clamps 22, 23 and 24.

A tube 25 leads from the upper end of the drip chamber 17 to a pressure meter 26 positioned in the apparatus 1.

The function of the above described infusion tube set is as follows. The tube segment 19 is laid in the housing of the peristaltic pump 3. The tube 25 is coupled to the pressure meter 26. The connector 21 is coupled to an infusion point, such as a drip chamber in the extracorporeal circuit. The connector 11 is coupled to a storage bag 4 of sterile infusion solution.

The tube clamp 22 is opened and the peristaltic pump 3 is started in order to suck air out of the tubes 18, 16 and 13, as well as permitting the sterile infusion solution to reach the drip chamber 17 and fill the tubes 13, 16, 18, and 20 as well as reach the connector 21 for infusion. The level in the drip chamber 17 is adjusted by temporarily opening the tube clamp 24 in the tube 9. Thereafter the tube set is ready for use. The peristaltic pump 3 pumps sterile infusion solution with the adjusted flow speed so that a desired total infusion volume will be supplied.

The pressure meter measures, via the tube 25, the pressure in the drip chamber. If the pressure drops below a predetermined limit, such as under −100 mm Hg, an alarm signal is emitted which indicates that the storage bag is empty.

If the tube 18 or 20 is folded such that fluid cannot pass, this cannot be detected by the machine. In order to make such an indication possible, the storage bag can, in a known embodiment, be placed on a scale which continually weighs the bag and emits an alarm signal if the weight does not drop in the desired manner. This embodiment with a scale is preferably used with larger infusion volumes where a plurality of storage bags are used and coupled to the connector 12 or additional connectors on the tube set.

According to the present invention a restriction device 30 is inserted into the tube 16 immediately before the drip chamber 17 (see FIG. 2) where the parts which are identical with FIG. 1 have been given the same reference numerals.

The restriction device 30 results in the pressure in the drip chamber 17 varying in proportion to the flow speed through the restriction device. With the aid of the pressure meter 26 the flow speed through the tube 16 can thus be measured and in this way also the flow speed through the connector 21.

The pressure in the drip chamber 17 is approximately inversely proportional to the flow speed. The apparatus 1 is provided with a processor which can have stored data for the relationship between the pressure in the drip chamber and the flow speed.

The restriction device can be manufactured as a separate unit with a very accurate predetermined hole size, so that the pressure drop is well defined. The restriction device can thereby be used for calibrating the peristaltic pump by a number of correlations being carried out at desired flow speeds, which can be done during priming or on other occasions.

Since the restriction device is a passive component, it can also sense if a tube would be blocked or if the pump was not pumping despite its rotor turning.

The restriction device can also be constituted as a tube segment with reduced internal diameter. Thus the tube 16, which is normally about 50 cm long and has an internal diameter of 3 mm, can be replaced with an equally long tube having an internal diameter of 0.5 mm.

Figure 3:
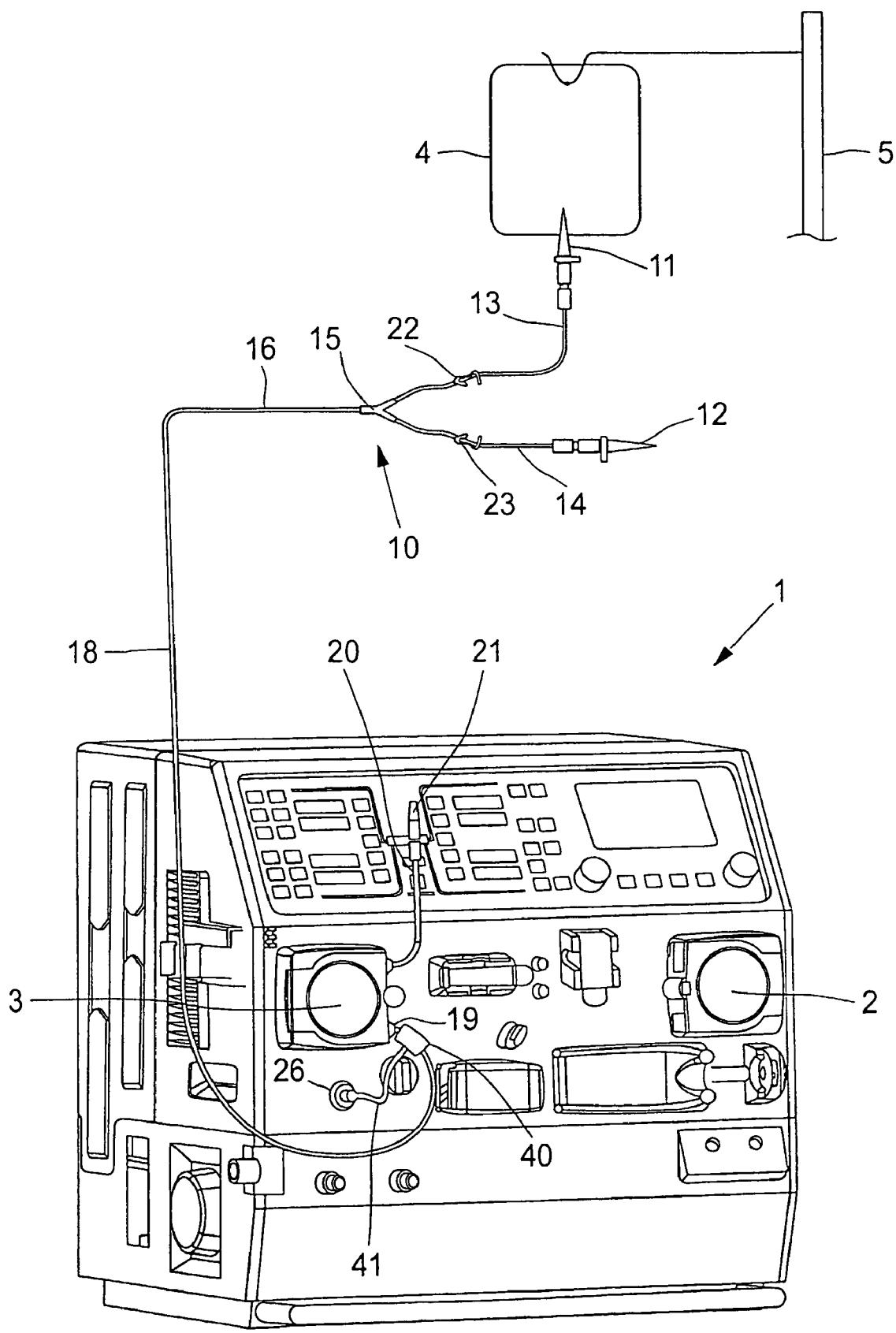
FIG. 3 is a view similar to FIG. 2 of an alternative embodiment of the invention.

In certain applications no drip chamber 17 is needed, especially when an air separating function is already present in the extracorporeal circuit. Such an embodiment is shown in FIG. 3.

Figure 2:
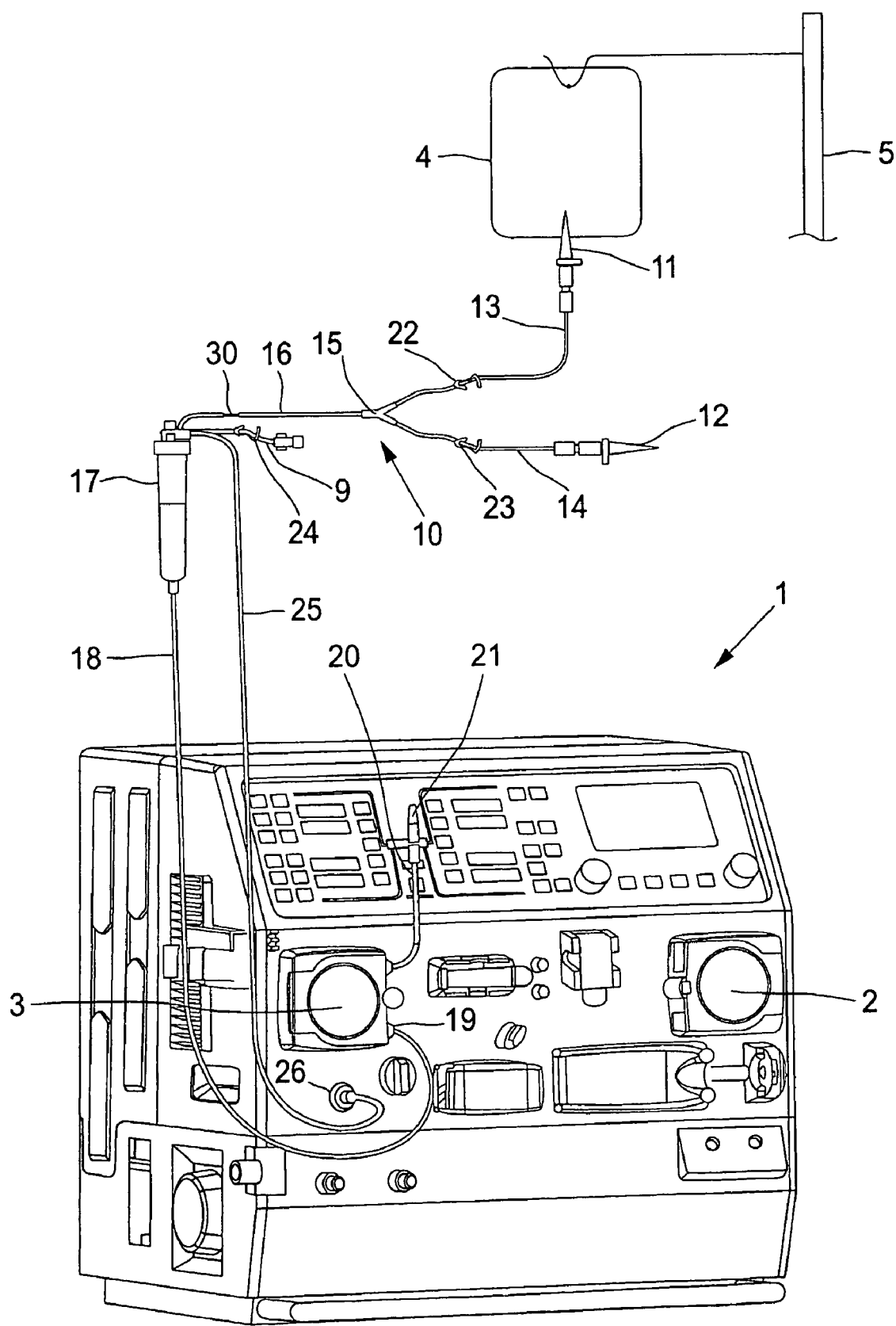
FIG. 2 is a view similar to FIG. 1 of a hemofiltration apparatus according to the invention.

Compared to the embodiment in FIG. 2, the drip chamber 17 and its tubing are removed and the tubes 16 and 18 now constitute a single tube. Just before the peristaltic pump segment 19 there is a T-coupling 40 which contains a restriction device and a branch coupling coupled to a tube 41 which leads to the pressure meter 26.

Figure 4:
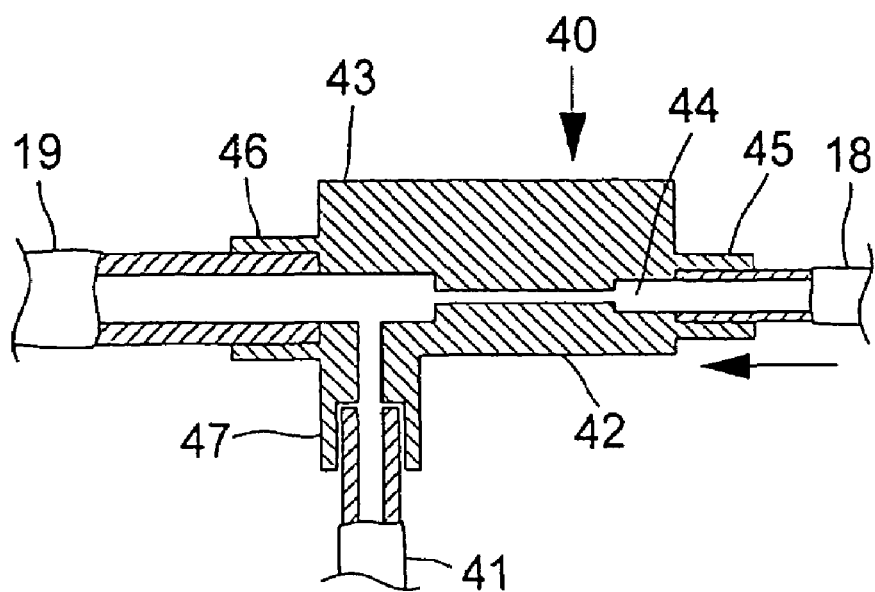
FIGS. 4 and 5 are cross-sectional views through a T-coupling in the embodiment of FIG. 3.

FIG. 4 shows an example of how the T-coupling can be constructed. The coupling comprises a housing 43 with a continuous bore 44, which has a severe constriction 42 that constitutes the actual restriction device. The tube 18 is coupled to a connector piece 45, the pump segment 19 is coupled to a connector piece 46 and the pressure tube 41 is coupled to a connector piece 47. As is clear from the Figures, the tube 41 can be thinner.

Figure 5:
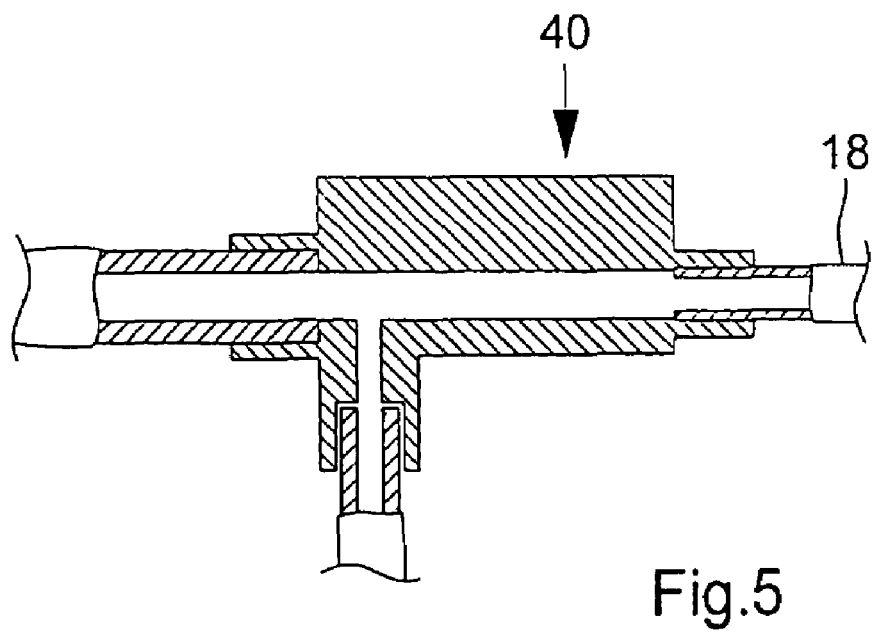

FIG. 5 shows an alternative construction of the T-coupling where the restriction function itself is built-in into the tube 18 in that its internal diameter is small. Alternatively the external diameter of tube 18 can of course be less, but then the risk of the tube 18 folding or becoming blocked is increased.

In the embodiment of FIG. 3 the pressure meter is well below the level of the storage bag. If then the pressure meter measures the pressure in respect to the surrounding pressure, the hydrostatic pressure has to be subtracted from the measured value. This is made possible by the pressure meter being read when the peristaltic pump is at a standstill and thus the flow is zero. The value which the pressure meter shows, e.g. about 40 mm Hg if the bag is about 53 cm above the pressure meter, should then be subtracted from the actual measured value. If the actual measured value is −20 mm Hg, the pressure difference consequently across the restriction device will be 60 mm Hg. If the actual value is +20 mm, the pressure difference across the restriction device will consequently be 20 mm Hg.

Several examples have been described above in connection with different embodiments. It is to be understood that the different features can each be combined in different ways than those described above, which is intended to be included in the invention.

The invention has been described in connection with a hemofiltration apparatus but can also be used in connection with hemodiafiltration, peritoneal dialysis and other medical treatment methods which include infusion.

What is claimed is:

1. A method for monitoring flow speed of an infusion solution, the method comprising:
    conducting the infusion solution from a closed source of infusion solution, via a tube to a pump device;
    arranging the source at a height with respect to a pressure-measuring device configured to provide a hydrostatic pressure;
    pumping the infusion solution to an infusion device;
    measuring with the pressure measuring device the hydrostatic pressure at zero flow of the infusion solution;
    starting a flow of infusion solution;
    restricting the flow of infusion solution so that the restricted flow rate is predetermined;
    measuring pressure in the infusion solution with the pressure-measuring device, the pressure-measuring device being arranged downstream of a location of flow restriction; and
    calculating flow speed of the infusion solution based upon the measured pressure, the predetermined restricted flow rate, and the hydrostatic pressure.

2. The method of claim 1, wherein restricting flow occurs using a restriction device arranged in an infusion solution conduit, the restriction device having a predetermined hole size.

3. The method according to claim 1, wherein flow speed of infusion solution is monitored during at least one of hemofiltration and hemodiafiltration.

4. The method according to claim 1, further comprising metering the infusion solution via said pump device, which comprises a metering pump.

5. The method according to claim 4, wherein the metering pump is a peristaltic pump.

6. The method according to claim 4, wherein the metering pump is a ceramic pump.

7. The method according to claim 6, wherein the sterile infusion solution is hemofiltration solution.

8. The method according to claim 1, wherein said source of infusion solution comprises at least one bag of sterile infusion solution.

9. The method according to claim 1, wherein the pressure measuring device measures the pressure with respect to surrounding atmosphere.

10. A device for monitoring flow speed of an infusion solution, the device comprising:
    a tube for conducting the infusion solution from a closed source of infusion solution to a pump device, where the source is arranged at a height with respect to a pressure measuring device for providing a hydrostatic pressure;
    a pump device for pumping the infusion solution to an infusion device;
    a restriction device having a predetermined hole size arranged in the tube, the pressure measuring device being arranged downstream the restriction device wherein the pressure measuring device is arranged to measure the pressure in the infusion solution at zero flow and at infusion flow, respectively; and
    a calculating device arranged to calculate the flow speed of the infusion solution based upon the measured pressure, the predetermined hole size in the restriction device, and the hydrostatic pressure.

11. The device according to claim 10, configured to monitor the flow speed of an infusion solution during at least one of hemofiltration and hemodiafiltration.

12. The device according to claim 10, wherein said pump comprises a metering pump for metering the infusion solution.

13. The device according to claim 10, wherein the metering pump is a peristaltic pump.

14. The device according to claim 13, wherein the sterile infusion solution is hemofiltration solution.

15. The device according to claim 10, wherein the metering pump is a ceramic pump.

16. The device according to claim 10, wherein said source of infusion fluid is at least one bag containing sterile infusion solution.

17. The device according to claim 10, wherein the pressure measuring device is arranged to measure the pressure with respect to surrounding atmosphere.

* * * * *

UNITED STATES PATENT AND TRADEMARK OFFICE
CERTIFICATE OF CORRECTION

PATENT NO. : 7,044,002 B2  Page 1 of 1
APPLICATION NO. : 10/258015
DATED : May 16, 2006
INVENTOR(S) : Ericson et al.

It is certified that error appears in the above-identified patent and that said Letters Patent is hereby corrected as shown below:

On the title page, item (73), "Ganbro" should read --Gambro--.

On the title page, item (73), "(CH)" should read --(SE)--.

Signed and Sealed this

Twenty-second Day of August, 2006

JON W. DUDAS
*Director of the United States Patent and Trademark Office*